US010538593B2

(12) United States Patent
Tsukamoto

(10) Patent No.: US 10,538,593 B2
(45) Date of Patent: Jan. 21, 2020

(54) METHOD FOR MANUFACTURING DIGESTIVE ENZYME ANTIBODY AND EGG HAVING SAME, AND FOR MANUFACTURING PROCESSED PRODUCT CONTAINING EGG AS INGREDIENT THEREOF AND COMPOSITION INCLUDING ANTIBODY

(71) Applicant: OSTRICH PHARMA KK, Kyoto (JP)

(72) Inventor: Yasuhiro Tsukamoto, Osaka (JP)

(73) Assignee: OSTRICH PHARMA KK, Kyoto (JP)

( * ) Notice: Subject to any disclaimer, the term of this patent is extended or adjusted under 35 U.S.C. 154(b) by 0 days.

(21) Appl. No.: 16/038,497

(22) Filed: Jul. 18, 2018

(65) Prior Publication Data

US 2018/0319896 A1     Nov. 8, 2018

Related U.S. Application Data

(63) Continuation-in-part of application No. 15/100,821, filed as application No. PCT/JP2014/006027 on Dec. 2, 2014, now Pat. No. 10,053,516.

(30) Foreign Application Priority Data

Dec. 2, 2013   (JP) ................................. 2013-249673
Aug. 22, 2014  (JP) ................................. 2014-169649

(51) Int. Cl.
| A61K 39/00 | (2006.01) |
| C07K 16/40 | (2006.01) |
| A61P 3/10  | (2006.01) |
| A23L 33/10 | (2016.01) |
| A61P 3/04  | (2006.01) |

(52) U.S. Cl.
CPC .............. *C07K 16/40* (2013.01); *A23L 33/10* (2016.08); *A61P 3/04* (2018.01); *A61P 3/10* (2018.01); *A23V 2002/00* (2013.01); *A61K 2039/505* (2013.01); *A61K 2039/507* (2013.01); *C07K 2317/23* (2013.01); *C07K 2317/76* (2013.01)

(58) Field of Classification Search
None
See application file for complete search history.

(56) References Cited

U.S. PATENT DOCUMENTS

| 7,344,713 B1 | 3/2008 | Pimentel |
| 10,053,516 B2 | 8/2018 | Tsukamoto |

| 2003/0087841 A1 | 5/2003 | Heinz et al. |
| 2006/0182730 A1 | 8/2006 | Kodama |
| 2009/0306347 A1 | 12/2009 | Tsukamoto |

FOREIGN PATENT DOCUMENTS

| JP | 9-313148 A       | 12/1997 |
| JP | 2001-521900 A    | 11/2001 |
| JP | 2011-20927 A     | 2/2011  |
| JP | 2012-224589 A    | 11/2012 |
| JP | 2013-147471 A    | 8/2013  |
| KR | 2003-0026046     | 3/2003  |
| KR | 2003-0079382     | 10/2003 |
| WO | WO 2004/089386 A1 | 10/2004 |
| WO | WO 2007/026689 A1 | 3/2007  |
| WO | WO 2010/041343 A1 | 4/2010  |
| WO | WO 2011/007792 A1 | 1/2011  |

OTHER PUBLICATIONS

Mai Hirose et al., "Shinki Ko Lipase Keiran Kotai ni yoru Ko Himan Sayo", The Japanese Society of Nutrition and Food science Taikai Koen Yoshishu, Apr. 27, 2014, vol. 66th, p. 127.
Shoka Koso, Seikagaku Jiten (3rd edition), 1998, pp. 691 to 692, column of Shoka Koso.
Dachoran de Metabo Taiji Kyoto Furitsu Daigaku ga Shoka Kyushu Osaeru Busshitsu, Kyoto Shinbun, Aug. 29, 2014.
International Search Report for corresponding International Application No. PCT/JP2014/006027 dated Mar. 17, 2015.
Shinki kou ripaze keiran koutai ni yoru kou himan sayou (Antiobesity effect of new anti-lipase hen egg antibody), Proceedings of Annual Meeting of Japan Society of Nutrition and Food Science, Apr. 27, 2014, vol. 66th p. 127, 2I-11p and English translation.

(Continued)

*Primary Examiner* — Marianne P Allen
(74) *Attorney, Agent, or Firm* — Renner, Otto, Boisselle & Sklar, LLP

(57) ABSTRACT

There are many reports of diseases caused by overeating, satiation, and an unbalanced diet, and various therapeutic methods and therapeutic drugs are proposed for said diseases. There have not been many proposals, for prevention of these diseases, of methods by which what is eaten is not readily absorbed in vivo. The present invention involves inoculating female birds with a digestive enzyme as an antigen, said digestive enzyme being present in vivo. As a result of inhibiting the activity of the digestive enzyme by using an antibody which has been produced in vivo in the birds, the present invention inhibits decomposition of proteins, lipids, and carbohydrates and reduces in vivo absorption. This type of antibody can be obtained from an egg laid by a female bird which has received the antigen, and furthermore the egg itself includes the antibody. Consequently, a food product that contains, as an ingredient thereof, eggs having this type of antibody is low in proteins, lipids, and carbohydrates. Furthermore, by ingesting the antibody obtained from the eggs, the absorption of proteins, lipids, and carbohydrates can be decreased.

3 Claims, 11 Drawing Sheets

(56) References Cited

OTHER PUBLICATIONS

Official Action for corresponding Japanese Application No. 2015-551393 dated Oct. 22, 2018 and its partial English translation.
Official Action for corresponding Japanese Application No. 2015-551393 dated May 13, 2019 and its partial English translation.
Official Action for corresponding Japanese Application No. 2019-010585 dated Sep. 12, 2019 and partial English translation.

[Fig. 1]
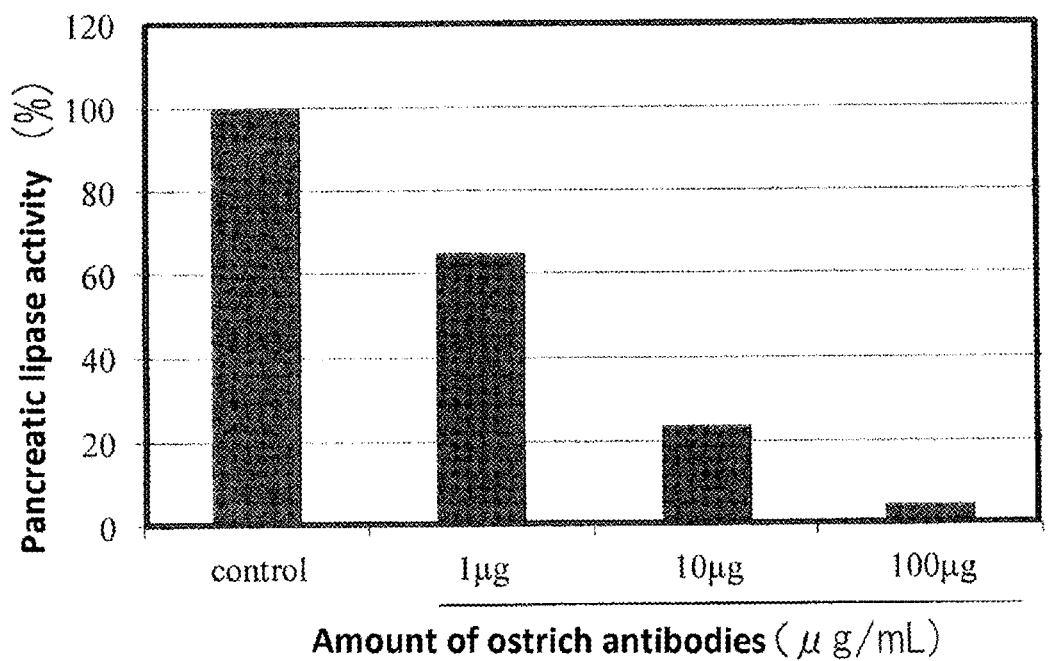

[Fig 2]
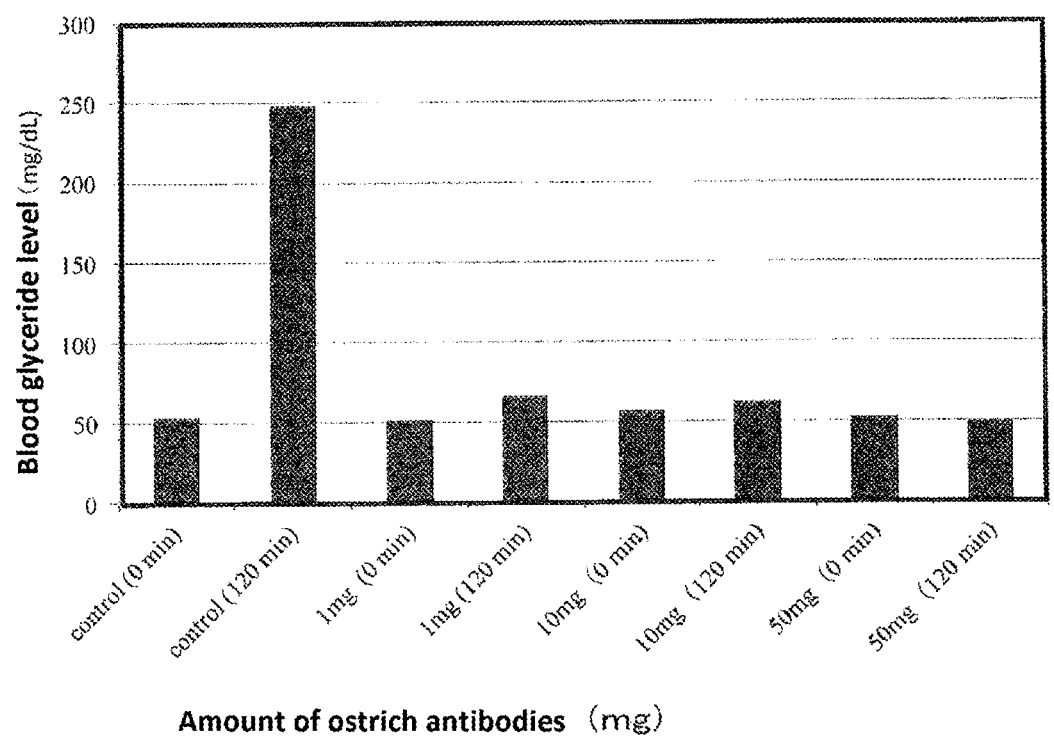

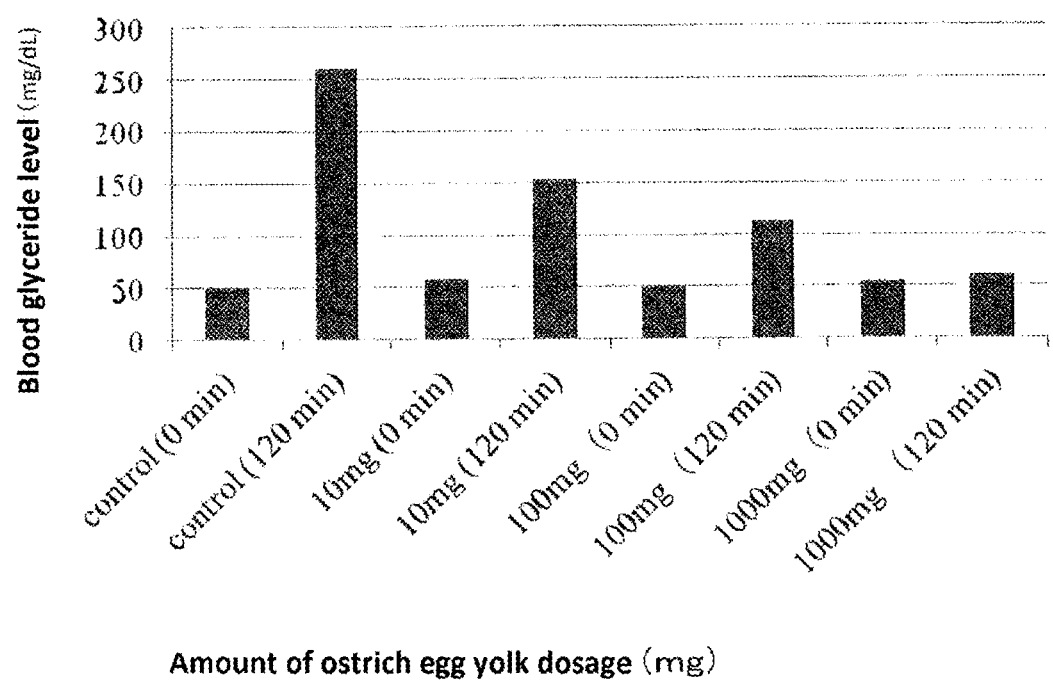

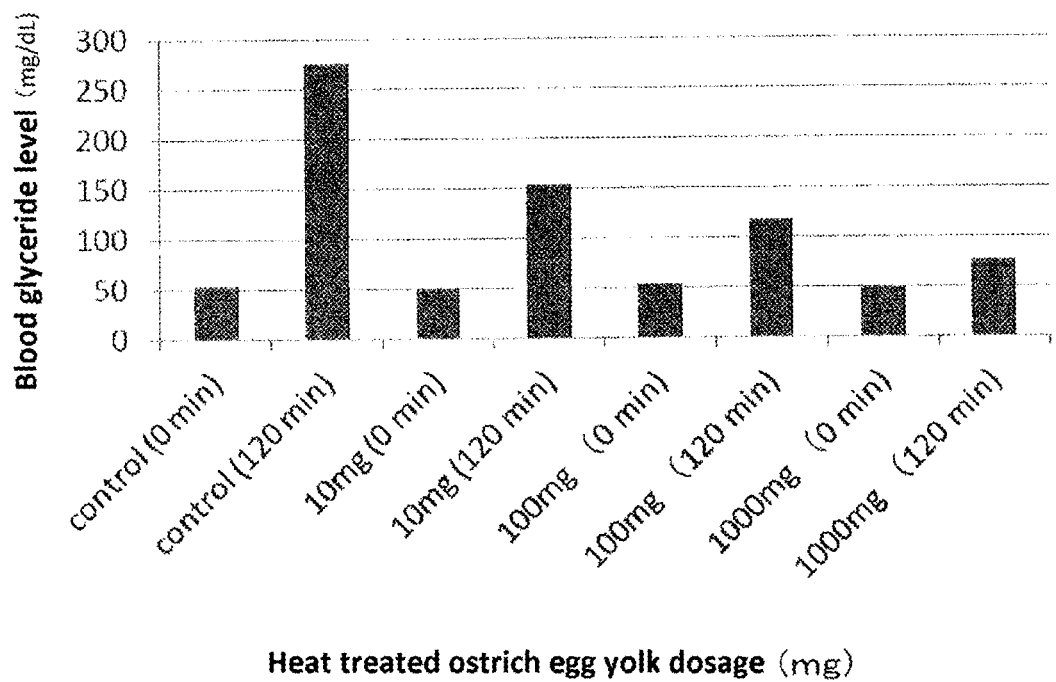
[Fig 4]

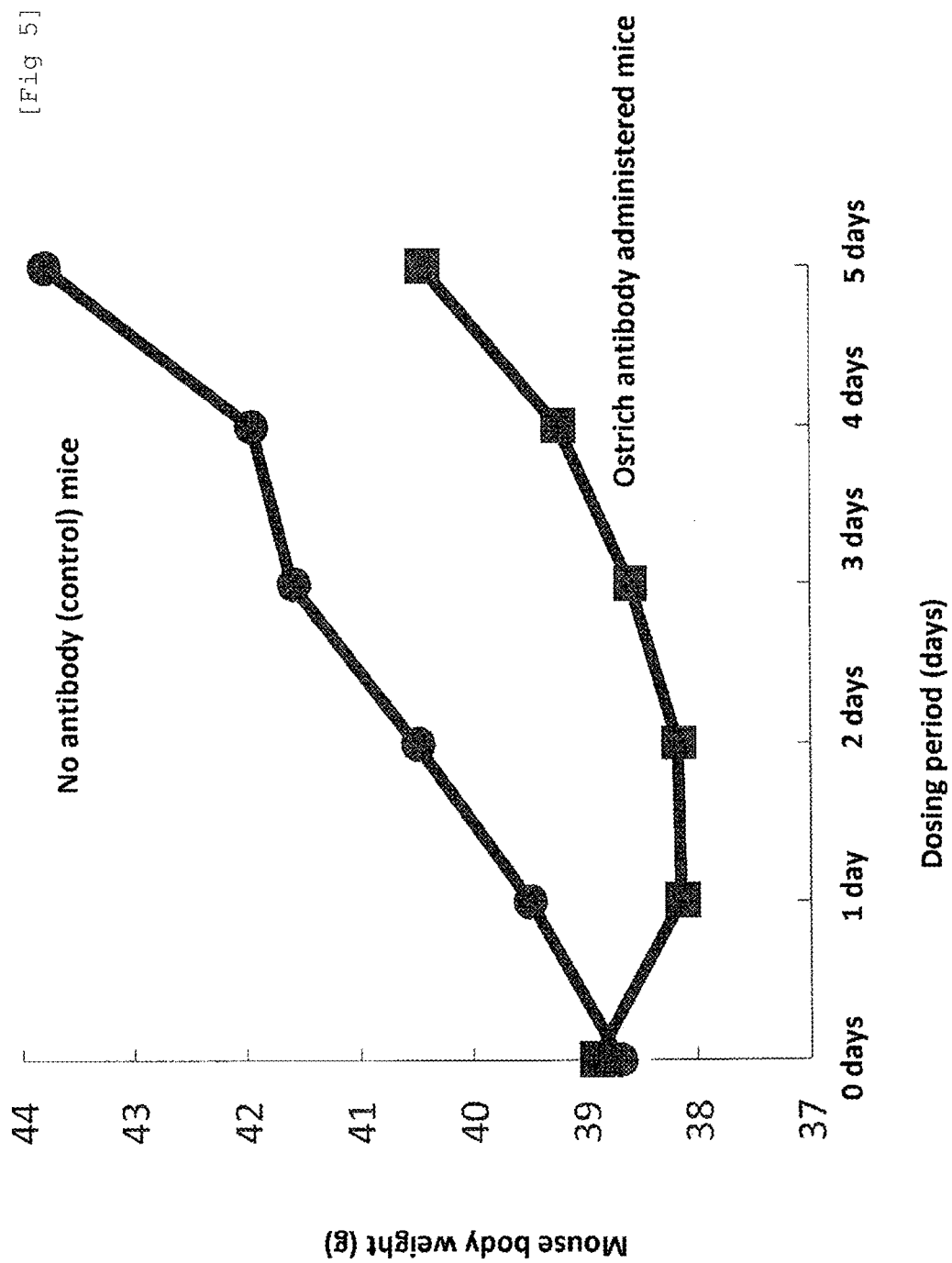

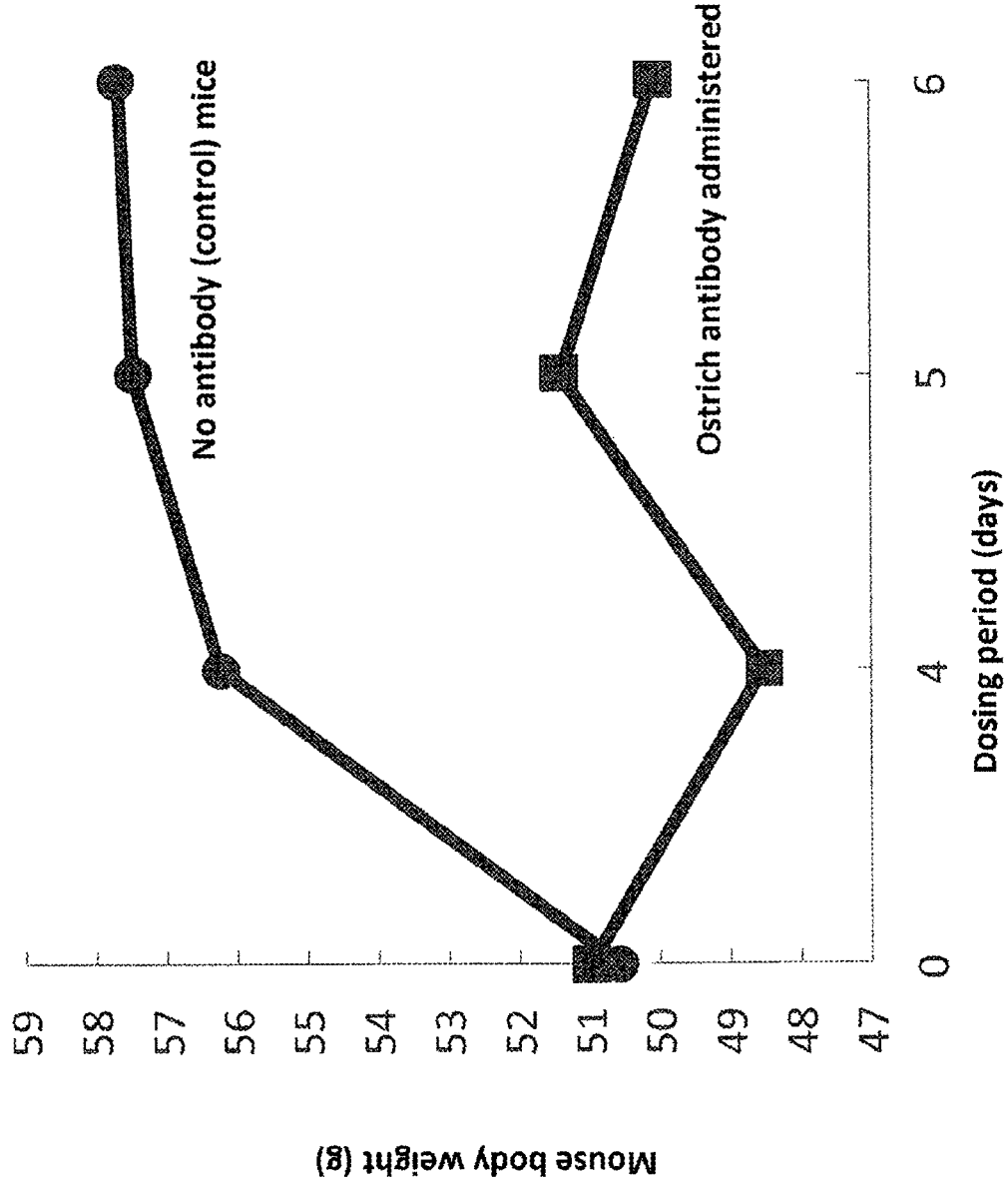

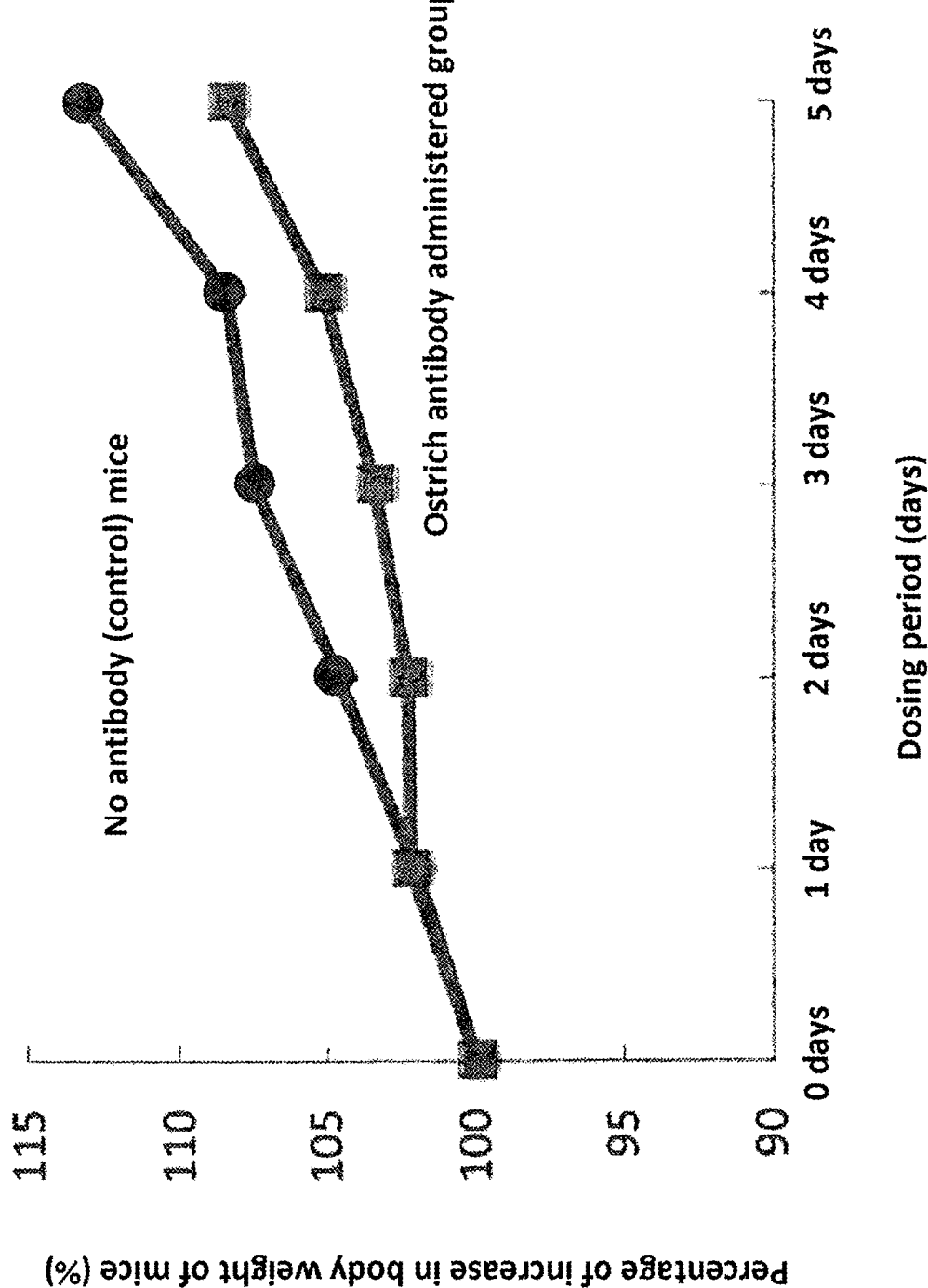

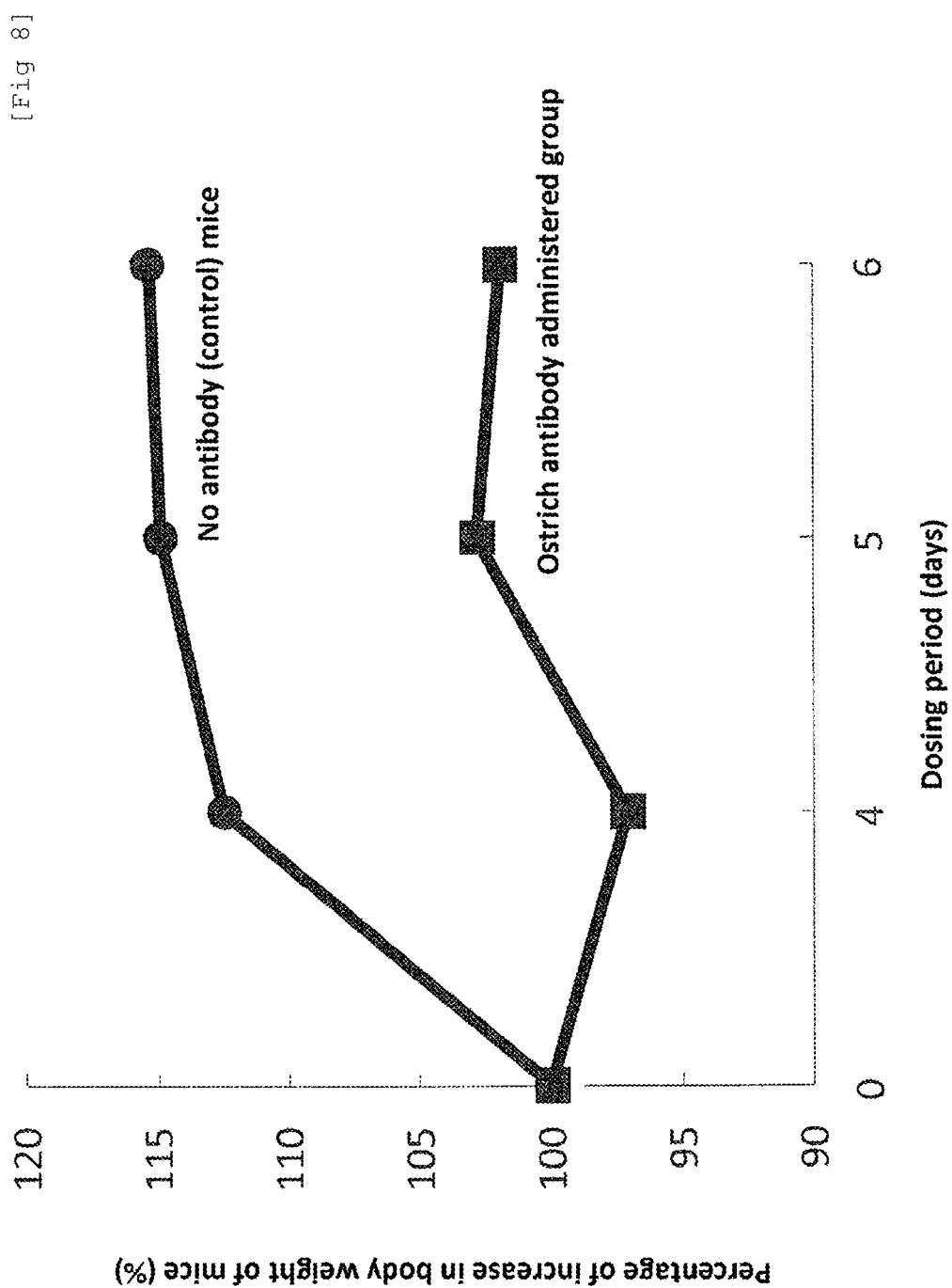

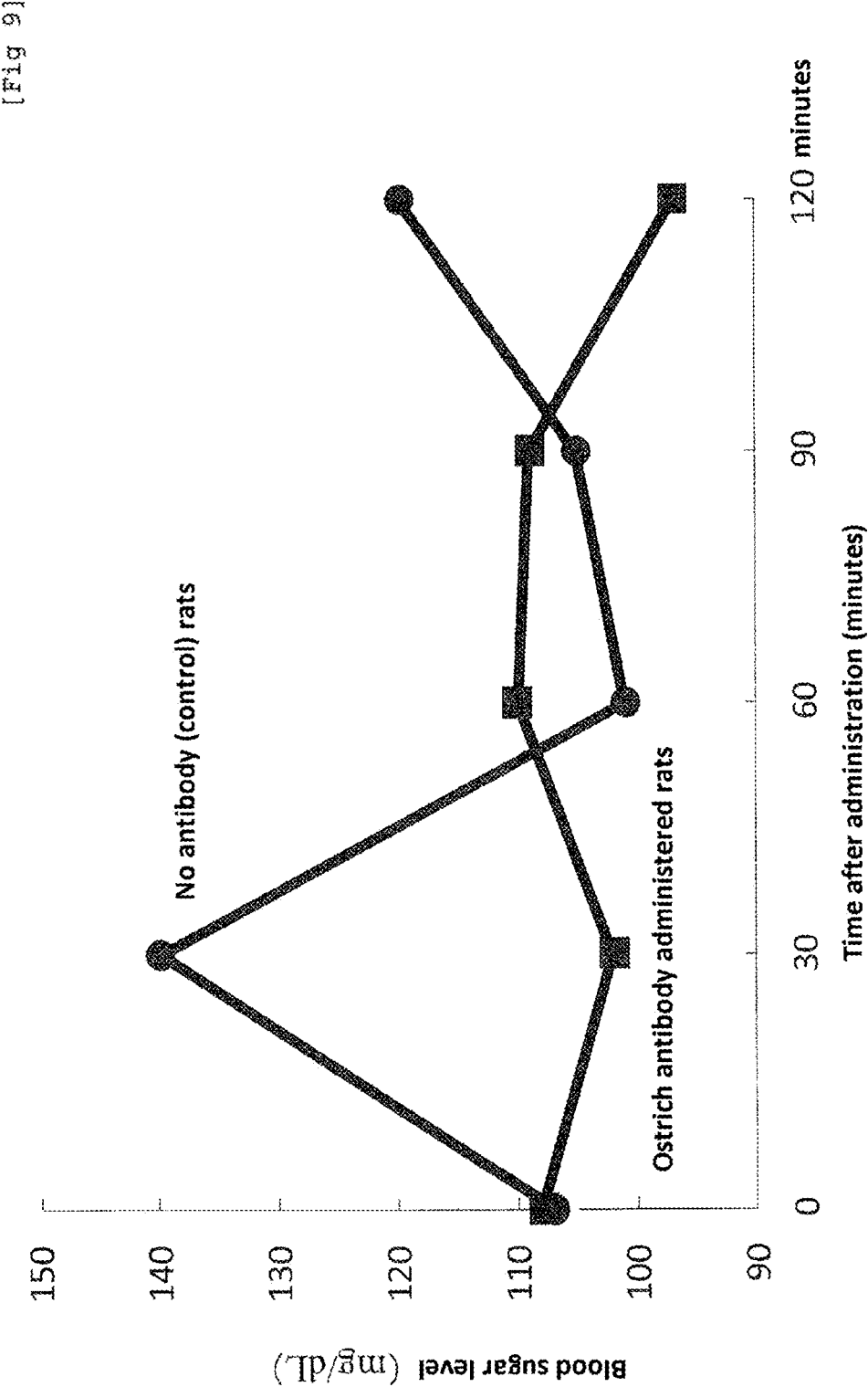
[Fig 9]

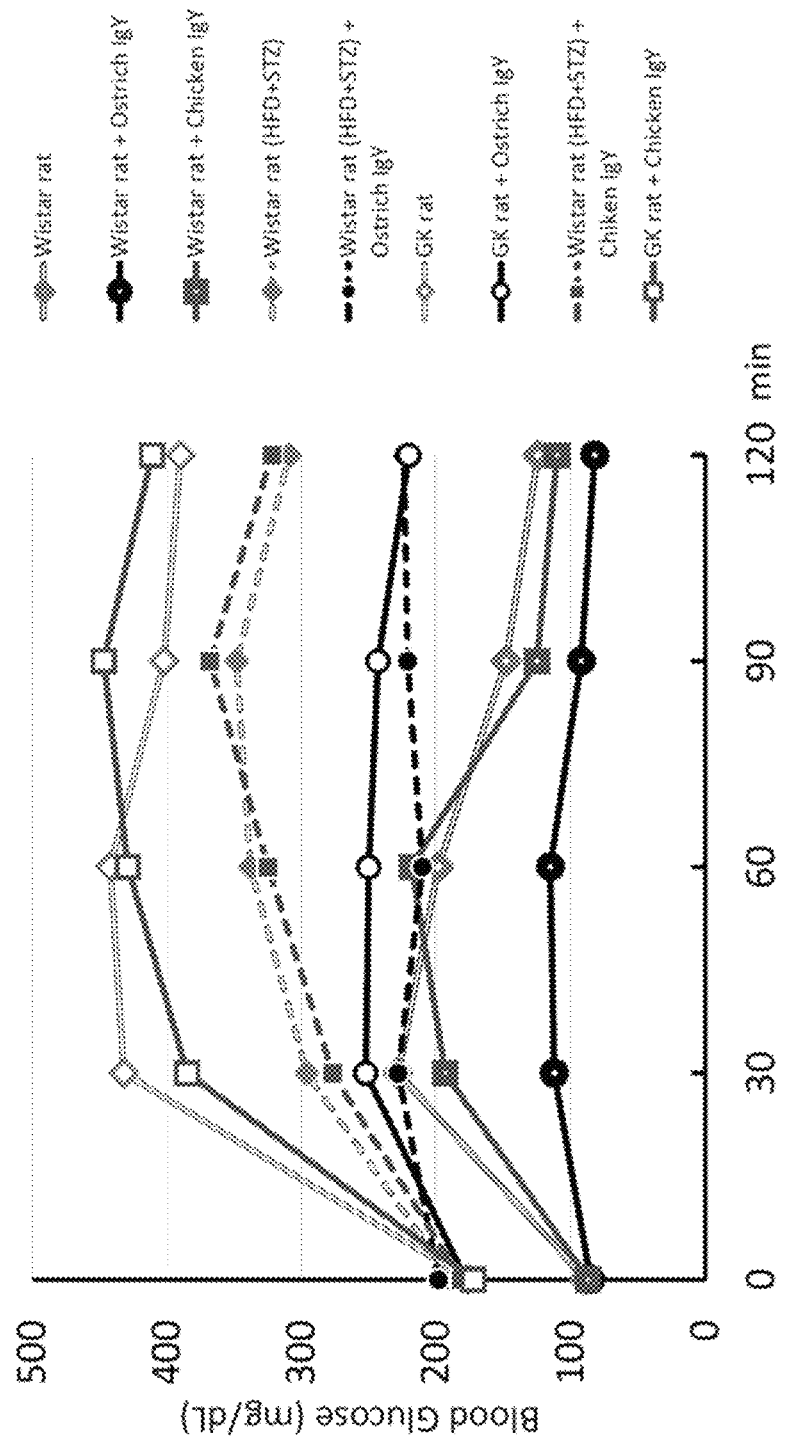
[Fig 10]

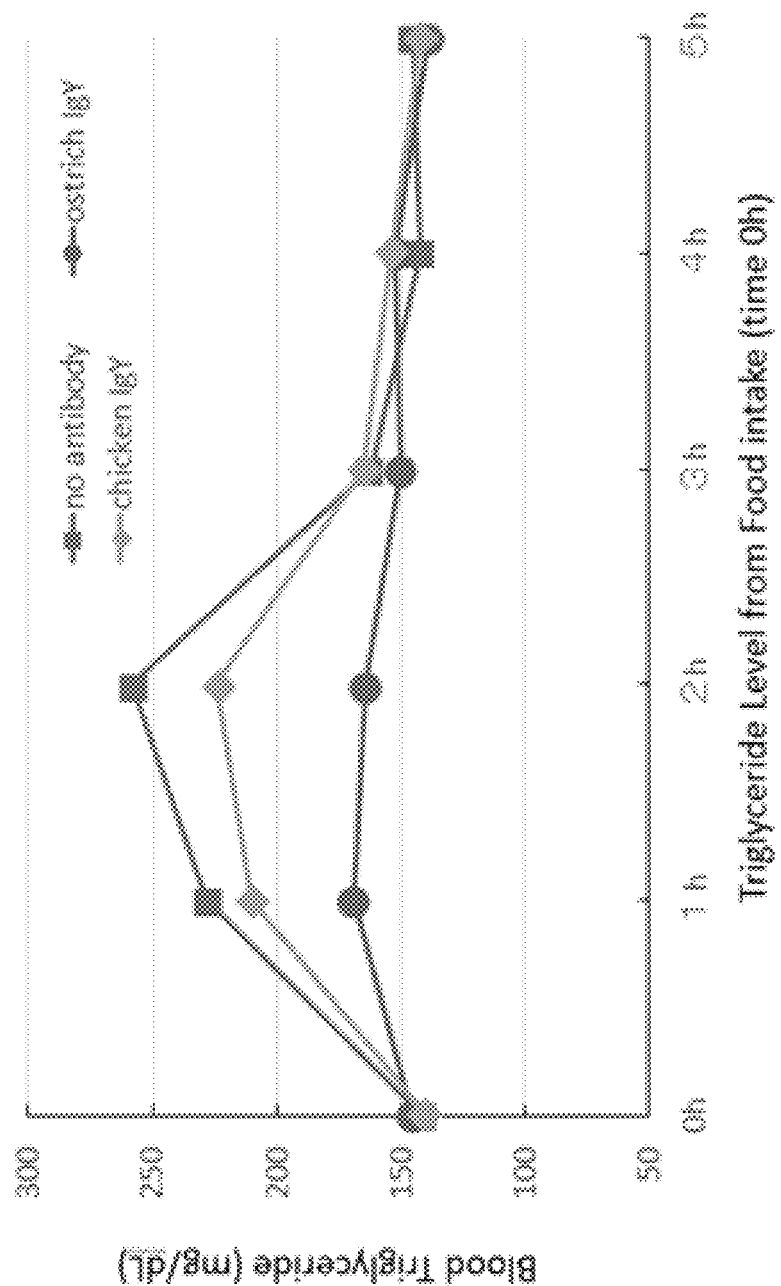

METHOD FOR MANUFACTURING DIGESTIVE ENZYME ANTIBODY AND EGG HAVING SAME, AND FOR MANUFACTURING PROCESSED PRODUCT CONTAINING EGG AS INGREDIENT THEREOF AND COMPOSITION INCLUDING ANTIBODY

TECHNICAL FIELD

The present invention relates to an antibody obtained with a digestive enzyme as an antigen and an egg having the antibody, processed product using the egg having the antibody as an ingredient, and a composition comprising the antibody.

BACKGROUND ART

Many cases of diseases due to overeating, gluttony, or unbalanced diet have been reported. Various therapeutic methods and therapeutic agents thereof have been proposed. Not many have proposed a method in which food, when eaten, is not readily absorbed.

Patent Literature 1 describes that guava leaf polyphenol suppresses sugar production during digestion/absorption, such that an efficacy of suppressing sugar absorption into the intestinal tract, preventing obesity effectively or the like can be expected.

Further, Patent Literature 2 describes that predetermined oxidoreductases such as flavin adenine dinucleotide-binding glucose dehydrogenase can catalyze a redox reaction with glucose as a substrate under an intragastric environment or intraintestinal conditions to reduce intragastric or intraintestinal glucose levels.

CITATION LIST

Patent Literature

[PTL 1] International Publication No. WO 2010/041343
[PTL 2] International Publication No. WO 2011/007792

SUMMARY OF INVENTION

Technical Problem

The methods disclosed in the Patent Literatures attempt to act on nutrients itself such as fats, carbohydrates, or proteins to reduce absorption thereof into the body.

Meanwhile, the process of absorption of nutrients into the body is considered to be as follows. Food is decomposed into the smallest units of molecules by an enzyme and absorbed by the intestinal tract. Fats are decomposed into fatty acid and glycerin, and the final products are absorbed by the intestinal mucosa as nutrients. Carbohydrates are ultimately decomposed into glucose by a carbohydrase such as maltase, lactase, or fructose and absorbed from the mucous membrane of the intestinal tract.

Further, proteins are decomposed into amino acids by a proteinase and absorbed by the intestinal tract. That is, food is not absorbed into the body and utilized as a nutrient unless it is digested by a digestive enzyme and decomposed into the smallest unit thereof. That is, fats and carbohydrates in food are not digested, but are excreted as excrements.

The present invention acts on a digestive enzyme itself to decrease digestive activity itself in the body with an antibody inhibiting enzymatic activity to reduce absorption of nutrients into the body.

Solution to Problem

More specifically, the antibody with a digestive enzyme as an antigen of the present invention is an egg characterized by being laid by female aves which are inoculated with the antibody with a digestive enzyme as an antigen and a processed product (including prepared meals) using the egg as an ingredient. The present invention is also a composition having an antibody obtained from such an egg.

Advantageous Effects of Invention

The antibody of the present invention can inhibit digestive enzyme function. An antibody with a specific digestive enzyme as an antigen can suppress absorption of a specific nutrient. As an example of application to patients with obesity or high levels of neutral fat, oral intake of an antibody against lipase (anti-lipase antibody) results in the binding of the antibody to the lipase in the digestive tract to suppress the function of lipase.

In addition, decomposition of fat in food is suppressed, resulting in less decomposition product of fat, i.e., glyceride. Thus, the amount of absorption from the intestine decreases to lower the blood glyceride level. That is, since absorption of fat is suppressed, hyperlipidemia can be improved and obesity can be prevented or improved.

Further, intake of an antibody against a carbohydrase (such as maltase, lactase, or fructase) can decrease the amount of carbohydrates decomposed into the final product, glucose, and reduce the amount of glucose absorbed from the intestine. Elevation in blood sugar levels can be suppressed thereby. Thus, diabetes patients can have a normal meal without worrying about blood sugar levels.

BRIEF DESCRIPTION OF DRAWINGS

FIG. 1 is a graph showing the relationship between the amount of ostrich antibodies and pancreatic lipase activity.
FIG. 2 is a graph showing the relationship between the amount of ostrich egg yolk antibodies and blood triglyceride level before and after administration.
FIG. 3 is a graph showing the relationship between the ostrich egg yolk dosage and blood triglyceride level before and after administration.
FIG. 4 is a graph showing the relationship between heat treated ostrich egg yolk dosage and blood triglyceride level before and after administration.
FIG. 5 is a graph showing increase in body weight when young mice are allowed anti-lipase antibody intake.
FIG. 6 is a graph showing increase in body weight when old mice are allowed anti-lipase antibody intake.
FIG. 7 is a graph converting FIG. 5 as percentage of increase in body weight.
FIG. 8 is a graph converting FIG. 6 as percentage of increase in body weight.
FIG. 9 is a graph showing the change in blood sugar levels when old rats are allowed anti-maltase/ostrich antibody intake.
FIG. 10 is a graph showing the change in blood glucose.
FIG. 11 is a graph showing the change in blood triglyceride.

DESCRIPTION OF EMBODIMENTS

The antibody of the present invention is explained hereinafter. The following explanation shows one embodiment of the present invention. The following embodiments and Examples may be modified within the intended scope of the present invention.

Targets of the antibody of the present invention are not particularly limited, as long as it is a digestive enzyme. Lipase, lactase, maltase, saccharase, amylase or the like can be preferably utilized. Further, a digestive enzyme is not limited to human digestive enzymes and may be a digestive enzyme of other organisms. For other organisms, mammals are more preferable. In one embodiment, the antibody of the subject invention comprises the antibodies against lipase, the antibodies against lactase, the antibodies against maltase, the antibodies against saccharase, or the antibodies against amylase. In other embodiment, the antibody of the subject invention comprises two or more of the antibodies against lipase, the antibodies against lactase, the antibodies against maltase, the antibodies against saccharase, or the antibodies against amylase. In the preferred embodiment, the antibody of the subject invention comprises the antibodies against lactase, the antibodies against maltase, the antibodies against saccharase, or the antibodies against amylase.

Further, aves that are used to produce an enzyme are not particularly limited. This is because aves and mammals have a low level of homology, and a mammalian digestive enzyme can be readily recognized as a foreign substance. Further, use of ostriches is more preferable, as a large amount of antibodies can be obtained in a single lot.

In the present invention, an egg itself, which is laid by female aves that are inoculated with a digestive enzyme as an antigen, can be utilized. This is because, for aves, antibodies produced in the body migrate to eggs. Further, antibodies are contained in both egg yolk and egg white. Thus, this can also be utilized in processed products including prepared meals utilizing only egg yolk or only egg white.

Particularly for ostriches, egg yolk antibodies are resistant to acidity or alkalinity and are highly heat resistant. Specifically, antibody activity is maintained even at 120° C. Antibody activity is also maintained in an intragastric low pH environment. Thus, antibody activity is not lost even when an egg is prepared as an egg dish such as a rolled omelet, fried egg, or pudding. Further, egg white used in creams, which is used in cakes, can also be used. It is also understood that the effect is exerted even when utilized in processed products such as mayonnaise.

Of course, antibodies purified from an egg can also be utilized as a digestive agent or digestion regulating agent. Antibodies may also be utilized in dosing, concurrently with other agents or the like. The antibodies can also be mixed into tea during a meal or utilized as sprinkled seasoning. In this manner, the antibody of the present invention can be utilized in any composition comprising the antibody of the present invention as one component thereof.

Intake of the antibody of the present invention before, after, or during a meal as a prepared meal using the antibody itself or an egg as an ingredient leads to the antibody adhering to a digestive enzyme in the digestive tract to inhibit enzymatic activity. As a result, digestion/decomposition into each nutrient is suppressed. Absorption of glyceride, glucose or the like can be suppressed as a result.

The antibody of the present invention can suppress absorption of only a specific nutrient by limiting digestive enzymes. Thus, the antibody can be widely utilized in patients with lifestyle diseases such as obesity, hyperlipidemia, or diabetes.

EXAMPLES

<Production of Antibody>

Mature female birds (ostriches, chickens, and quails) were used. 50 µg of antigens (lipase, lactase, maltase, saccharase, and amylase) were each mixed with 0.2 mL of Freund's Complete Adjuvant to prime the ostriches. Five ostriches, five chickens, and five quails were individually inoculated with each antigen. The ostriches, chickens, and quails were inoculated with the same amount of antigens.

After priming, each bird was boosted with a mixture solution of 50 µg of antigen and Freund's Incomplete Adjuvant in week 2 and week 4. Egg yolk antibodies (IgY) were purified from the egg yolk of eggs from each bird obtained in week 8 after priming. The reactivity of the obtained egg yolk antibodies was tested by ELISA (Enzyme-Linked Immuno Sorbent Assay).

Antibodies were purified by the following procedure. Specifically, first, to the egg yolk of the obtained eggs, 5 times the amount of TBS (20 mM of Tris-HCl, 0.15 M of NaCl, 0.5% $NaN_3$) and the same amount of 10% dextran sulfate/TBS were added, and the mixture was stirred for 20 minutes.

1M of $CaCl_2$/TBS was then added in the same amount as the egg yolk, and the mixture was stirred and left standing for 12 hours. The mixture was then centrifuged for 20 minutes at 15000 rpm, and the supernatant was collected. In addition, ammonium sulfate was added such that the final concentration would be 40%, and the mixture was left standing for 12 hours at 4° C.

After the mixture was left standing for 12 hours, the mixture was centrifuged for 20 minutes at 15000 rpm, and precipitates were collected. Finally, the precipitates in the same amount as the egg yolk were resuspended in TBS, and dialysis was performed with TBS. Antibodies (IgY) with a purity of 90% were able to be collected from each egg by the above method.

<Test by ELISA>

Reactivity of each antibody to a digestive enzyme was examined as follows. Solid phases of 10 µg of each antigen (lipase, lactase, maltase, saccharase, and amylase) were formed separately at each well of a 96-well ELISA plate (4 hours at room temperature). Serially diluted solutions (undiluted solution is 2 mg/mL) of ostrich antibodies (mixture of antibodies from the egg yolk obtained from each of the 3 ostriches), chicken antibodies (mixture of antibodies from the egg yolk obtained from each of the 3 chickens), and quail antibodies (mixture of antibodies from the egg yolk obtained from each of the 3 quails) were then dripped into each well and reacted for 1 hour at room temperature.

After washing, HRP labeled-secondary antibodies for each antibody were reacted for 1 hour at room temperature. After thoroughly washing, a luminescent peroxidase assay kit (S-Bio SUMILON) was used to measure absorbance (450 nm) with a plate reader. The maximum dilution factor indicating 2 times the absorbance value or greater of egg yolk antibodies of each avian species prior to immunization are shown as the ELISA value.

TABLE 1

| Antigen | ELISA value of egg yolk antibodies made from each aves | | |
|---|---|---|---|
| | Ostrich | Chicken | Quail |
| Lipase | 102,400 | 12,800 | 6,400 |
| Lactase | 51,200 | 25,600 | 12,800 |
| Maltase | 51,200 | 12,800 | 6,400 |
| Saccharase | 102,400 | 12,800 | 25,600 |
| Amylase | 102,400 | 6,400 | 12,800 |

It was found that egg yolk antibodies with a high level of sensitivity were made by immunizing ostriches, chickens, and quails with each of lipase, lactase, maltase, saccharase, and amylase. Although each avian species was immunized with the same amount of antigens, large-sized ostriches in particular produced antibodies with the highest reactivity. This indicates that highly sensitive antibodies can be produced with a small amount of antigens when an ostrich is used.

Next, the effect of antibodies was examined.

<Inhibitory Action of Ostrich Antibodies (Anti-Lipase Antibodies) on Pancreatic Lipase Activity>

Pancreatic lipase activity was calculated by measuring the amount of freed oleic acid from triolein. 80 mg of triolein (SIGMA), 10 mg of lecithin (Wako Pure Chemical Industries), and bile acid (SIGMA) were sonicated for 10 minutes in 9 ml of 0.1 M Tris buffer (pH 7.0) to prepare a homogeneous suspension, which was used as a substrate solution.

The experiment was carried out as follows. 0.05 ml of pancreatic lipase solution derived from a pig (SIGMA) (final concentration 1 µg/ml) and 0.1 ml of ostrich antibody solution were added to 0.1 ml of substrate solution and reacted for 30 minutes at 37° C. The freed fatty acid was quantified by a method using a copper reagent. The activity level of each specimen (ostrich antibody solution 1 µg, 10 µg, and 100 µg/mL) was calculated while setting the activity level when no ostrich antibody is added (control) as 100%.

The results are shown in FIG. 1. The horizontal axis indicates different types of amounts of ostrich antibodies (µg/mL) and control (amount of ostrich antibodies is 0) and the vertical axis indicates pancreatic lipase activity (%). The activity of pancreatic lipase decreased as the amount of ostrich antibodies increased. Thus, it was found that ostrich antibodies against lipase inhibit pancreatic lipase activity (i.e., digestion/decomposition of fat) in a concentration dependent manner.

<Effect of Ostrich Antibodies (Anti-Lipase Antibodies) on Variation in Neutral Fat in Rat Plasma after Loading Corn Oil>

Rats were separated into 4 groups of 6 rats, i.e., control group and ostrich antibody administered groups (1, 10, and 50 mg/rat) and starved overnight to conduct a corn oil loading experiment. Rats in the control group were orally administered a mixture solution of 1 ml of corn oil emulsion and 50 mg of preimmunization antibodies without anesthesia.

Rats in the ostrich antibody administered groups were administered with a mixture solution of 1 ml of corn oil emulsion and ostrich antibody solution. Blood was drawn from the caudal vein of the rats immediately prior to corn oil administration (0 min) and 120 minutes after administration (120 min) without anesthesia. Neutral fat content in plasma was measured by using Triglyceride E-test kit from Wako Pure Chemical. The values in the graph indicate the mean value of 6 rats in each group.

The results are shown in FIG. 2. The horizontal axis indicates different types of amounts of ostrich antibodies (mg) for immediately before administration of corn oil (0 min) and (120 min). The control is the case where the amount of ostrich antibodies is 0 (mg). Further, the vertical axis indicates the blood triglyceride level (mg/dL).

In the control group, the blood triglyceride level increased about 5 fold at 120 minutes after intake of corn oil. In the ostrich antibody administered groups, however, increase in blood triglyceride level after corn oil intake was significantly suppressed. A dramatic suppression effect was found even with a low dose (1 mg).

Intake of ostrich antibodies made by lipase immunization resulted in lipase activity inhibition and suppression of digestion/decomposition of fats into triglyceride. Thus, it is concluded that absorption from the intestinal tract is suppressed, resulting in suppression of increase in blood triglyceride levels.

<Effect of Ostrich Egg Yolk (Containing Anti-Lipase Antibodies) on Variation in Neutral Fat in Rat Plasma after Loading Corn Oil>

The ostrich egg yolk used was egg yolk (raw) from eggs (week 8 after priming) of ostriches immunized with lipase. Rats were separated into 4 groups of 6 rats, i.e., control group and ostrich egg yolk administered groups (10, 100, and 1000 mg/rat) and starved overnight to conduct a corn oil loading experiment. In the control group, rats were orally administered a mixture solution of 1 ml of corn oil emulsion and 1000 mg of preimmunization egg yolk without anesthesia.

Rats in the ostrich antibody administered groups were administered with a mixture solution of 1 ml of corn oil emulsion and ostrich egg yolk. Blood was drawn from the caudal vein of the rats immediately prior to corn oil administration (0 min) and 120 minutes after administration (120 min) without anesthesia. Neutral fat content in plasma was measured by using Triglyceride E-test kit from Wako Pure Chemical. The values in the graph indicate the mean value of 6 rats in each group.

The results are shown in FIG. 3. The horizontal axis indicates different types of ostrich egg yolk dosages (mg) for immediately before administration of corn oil (0 min) and (120 min). The control is the case where the ostrich egg yolk amount is 0 (mg). Further, the vertical axis indicates the blood triglyceride level (mg/dL).

In the control group, the blood triglyceride level increased about 5 fold at 120 minutes after intake of corn oil. In the ostrich egg yolk administered groups, however, increase in blood triglyceride level after corn oil intake was significantly suppressed in an egg yolk amount dependent manner. A dramatic suppression effect was found even with a low dose (10 mg).

Intake of egg yolk obtained from ostriches after lipase immunization resulted in lipase activity inhibition and suppression of digestion/decomposition of fats into triglyceride. Thus, it is concluded that absorption from the intestinal tract is suppressed, resulting in suppression of increase in blood triglyceride levels. In this manner, intake of egg yolk itself can also inhibit the activity of a digestive enzyme in the present invention.

<Effect of Heat Treated Ostrich Egg Yolk (Containing Anti-Lipase Antibodies) on Variation in Neutral Fat in Rat Plasma after Loading Corn Oil>

The ostrich egg yolk used was heat-treated (120° C. for 10 minutes) egg yolk (raw) from eggs (week 8 after priming) of ostriches immunized with lipase. Rats were separated into group of 6 rats, i.e., control group and heat treated ostrich egg yolk administered groups (10, 100, and 1000 mg/rat) and starved overnight to conduct a corn oil loading experiment. In the control group, rats were orally administered a mixture solution of 1 ml of corn oil emulsion and 1000 mg of preimmunization egg yolk without anesthesia.

Rats in the heat treated ostrich egg yolk administered groups were administered with a mixture solution of 1 ml of corn oil emulsion and heat treated ostrich egg yolk. Blood was drawn from the caudal vein of the rats immediately prior to corn oil administration (0 min) and 120 minutes after administration (120 min) without anesthesia. Neutral fat content in plasma was measured by using Triglyceride E-test kit from Wako Pure Chemical. The values in the graph indicate the mean value of 6 rats in each group.

The results are shown in FIG. 4. The horizontal axis indicates different types of heat treated ostrich egg yolk dosages (mg) for immediately before administration of corn oil (0 min) and (120 min). The control is the case where the heat treated ostrich egg yolk dosage is 0 (mg). Further, the vertical axis indicates the blood triglyceride level (mg/dL).

In the control group, the blood triglyceride level increased about 5 fold at 120 minutes after intake of corn oil. In the heat treated ostrich egg yolk dosage groups, however, increase in blood triglyceride level after corn oil intake was significantly suppressed in a heat treated egg yolk amount dependent manner. A dramatic suppression effect was found even with a low dose (10 mg).

Intake of egg yolk obtained from an ostrich after lipase immunization resulted in lipase activity inhibition and suppression of digestion/decomposition of fats into triglyceride. Thus, it is concluded that absorption from the intestinal tract is suppressed, resulting in suppression of increase in blood triglyceride levels. Furthermore, the egg yolk maintains the effect even after heat treatment. That is, sufficient suppression of increase in blood triglyceride level is observed even from intake of cooked ostrich egg. Thus, it is considered that food prepared with eggs of lipase immunized ostriches leads to prevention of hyperlipidemia and prevention or improvement in obesity.

<Obesity Suppressing Effect>

Young and old mice were allowed to voluntarily intake food with high fat content and ostrich egg yolk antibody solution (anti-lipase antibody) (added to drinking water) and the body weight thereof was measured over time. More specifically, each of the groups are: group of young mice allowed to intake anti-lipase antibodies (6 rats), group of young mice not allowed to intake anti-lipase antibodies (6 rats), group of old mice allowed to intake anti-lipase antibodies (6 rats), and group of old mice not allowed to intake anti-lipase antibodies (6 rats).

In this context, young mice are mice with a body weight of about 39 g, and old mice are mice with a body weight of about 51 g. The food with high fat content given to the mice was a commercially available product comprising 40% beef tallow (Oriental Yeast Co., Ltd: Product number AIN76). The method of intake was by voluntary intake.

When feeding food with high fat content, group of mice that were not allowed to intake anti-lipase antibodies were allowed to voluntarily intake PBS (Phosphate buffered saline). Further, the group of mice allowed to intake anti-lipase antibodies was allowed to voluntarily intake anti-lipase/ostrich antibody solution (15 mg/mL PBS). The body weight was measured over time from the start of administration of food with high fat content to calculate the mean body weight of all rats (6 rats) in each group.

The results are shown in FIGS. 5 and 6. FIG. 5 is a result for young mice, and FIG. 6 is a result for old mice. Each vertical axis indicates the dosing period (days), and each vertical axis indicates the body weight of mice (g). Circular marks were used as plots for mice not allowed to intake anti-lipase antibodies (described as "No antibody (control) mice" in the Figure) and squares were used as plots for mice allowed to intake anti-lipase antibodies (described as "Ostrich antibody administered mice" in the Figure).

Referring to FIGS. 5 and 6, drastic increase in body weight from intake of food with high fat content was observed in young and old mice that were not allowed to intake anti-lipase antibodies. However, increase in body weight was suppressed in mice, regardless of young or old, with ostrich antibody intake.

FIGS. 7 and 8 show results of FIGS. 5 and 6 when the vertical axis is converted to percentage of increase in body weight (%). FIG. 7 is a result for young mice, and FIG. 8 is a result for old mice. The horizontal axis indicates the dosing period (days) as in FIGS. 5 and 6.

Referring to FIG. 7, the effect of suppressing the percentage of increase in body weight in the cases of young mice was about 5% for no-antibody (control) mice. However, referring to FIG. 8, the effect of suppressing the percentage of increase in body weight was close to 15% in the cases of old mice. Old mice are considered to have lower basal metabolism relative to younger mice. Intake of food with high fat content is thus manifested as a dramatic increase in body weight. Anti-lipase antibodies suppress fat absorption in such a case. That is, the anti-lipase antibodies of the present invention are recognized to be particularly effective in suppressing obesity in individuals with decreased basal metabolism.

<Effect of Suppressing Elevation in Blood Sugar Level Due to Ostrich Antibody Intake>

Carbohydrates, when ingested, are digested and decomposed by a carbohydrate digestive enzyme to the smallest unit, glucose. Glucose intake by the capillaries in the mucous membrane of the intestinal tract elevates the blood glucose level (blood sugar level). The blood sugar level returns to a normal level thereafter due to insulin secretion. In diabetes, elevation in blood sugar levels is pronounced after food consumption and the subsequent return to a normal level is also incomplete. It is understood that suppression of elevation in blood sugar levels after food consumption would lead to prevention of exacerbation of diabetes.

In this regard, suppression of elevation in blood sugar levels after food consumption was attempted using antibody against carbohydrate digestive enzymes made from an ostrich. Old rats were orally administered b.w. with 1 g/kg of high concentration carbohydrate solution (main ingredient: maltose), and orally administered with ostrich antibodies immediately thereafter. Blood was then drawn from the caudal vein over time to measure the blood sugar levels (redox reaction by glucose oxidase activity). Please note that old rats refer to rats that are about 2 years old or older and close to the end of their lifespan.

No-antibody (considered as the control) rats were given PBS solution with 0.5 g/mL of maltose. Meanwhile, antibody administered mice were given 0.5 g/mL of maltose and solution with 20 mg/mL of anti-maltase/ostrich antibodies.

The results are shown in FIG. 9. The horizontal axis indicates the time after administration (minutes) and the vertical axis indicates blood sugar level (mg/dL). Circular marks are used as plots for no-antibody rats. Squares are used as plots for antibody administered rats. Blood sugar levels were transiently elevated after carbohydrate intake in no-antibody rats. However, elevation in blood sugar levels was significantly suppressed for ostrich antibody administered rats. In view of the above, intake of anti-maltase/ostrich antibodies concurrently with maltose intake is considered to have suppressed digestion of carbohydrates and resulted in lower amount of glucose absorption.

<Effect by Combination of Ostrich Antibodies (1)>

Two types of model rats, Wister rat, and GK rat (Type 2 diabetic model rat derived from Wister rat) were used in the experiment. The rats were separated into three test groups: (1) Type 2 diabetes Wister rat; (2) Type 2 diabetes GK rat; and (3) Wild type Wister rat as control.

In the first experiment, at time 0, all three test groups were orally administered with high calorie diet along with (A) Ostrich IgY solution against Amylase, Lactase, Saccharase and Maltase, (B) Chicken IgY solution against Amylase, Lactase, Saccharase and Maltase, or (C) without any antibody. Wherein for Ostrich IgY, each IgY dosage was 0.25 mg per animal, and for Chicken IgY, each IgY dosage was 1 mg per animal. Blood glucose was measured at 120 minutes after food and antibody intake. The blood glucose levels were compared between the groups over time.

The results are shown in FIG. 10. In all three test groups (Wild type Wister rat, diabetic Wister rat and diabetic GK rat), rat administered with Ostrich IgY showed the greatest suppression of elevation in blood glucose level at all time points (30, 60, 90 and 120 minutes). In contrast, the levels of suppression of elevation in blood glucose level were similar between rat administered with chicken IgY and rat without any antibody administration.

<Effect by Combination of Ostrich Antibodies (2)>

In this experiment, only wild type Wister rat model was used, the procedure of the above described experiment (<Effect by combination of ostrich antibodies (1)>) was repeated with the exception that blood triglyceride level was measured at 5 hours, rather than 120 minutes, after food and antibody intake.

The results are shown in FIG. 11. Wild type Wister rat administered with Ostrich IgY showed the greatest suppression of elevation in blood triglyceride level between minute and 3 hours after antibody administration as compared to rat administered with chicken IgY and rat without any antibody administration. It should be noted that the blood triglyceride level was increased by food intake within about 2 hours, and became normal after about 3 hours, as increased blood triglyceride was absorbed by the intestine. It is important to reduce the increase of blood triglyceride level immediately after food intake. For this purpose, Ostrich IgY is better than chicken IgY or control.

INDUSTRIAL APPLICABILITY

The antibody of the present invention is present in egg yolk and egg white of an egg. Thus, excessive calorie intake is suppressed by selecting and using either the egg yolk or egg white in a meal to be prepared. Further, intake of purified antibodies before and after a meal can inhibit absorption of a specific nutrient into the body. The antibodies can be mixed into not only pharmaceutical agents, but also into non-staple food such as tea, sprinkled seasoning, or other seasonings.

The invention claimed is:

1. A method for suppressing elevation in blood sugar level in a subject, comprising orally administering ostrich antibodies against digestive enzymes as an antigen to the subject,
    wherein the digestive enzymes comprise lactase, maltase, saccharase, and amylase, and
    wherein the ostrich antibodies are produced against a mixture of the digestive enzymes.

2. The method of claim 1, comprising orally administering the ostrich antibodies with meal to the subject.

3. The method of claim 1, wherein the mixture of the digestive enzymes further comprises lipase.

* * * * *